United States Patent [19]

Kompis et al.

[11] Patent Number: 5,721,242
[45] Date of Patent: Feb. 24, 1998

[54] ANTIBIOTIC COMBINATION

[75] Inventors: Ivan Kompis, Oberwil, Switzerland; Rudolf Then, Weil am Rhein, Germany

[73] Assignee: Hoffmann-La Roche Inc., Nutley, N.J.

[21] Appl. No.: 241,887

[22] Filed: May 12, 1994

[30] Foreign Application Priority Data

Jun. 17, 1993 [CH] Switzerland ............... 1801/93

[51] Int. Cl.$^6$ .................. A61K 31/505; A61K 31/135
[52] U.S. Cl. ................................ 514/272; 514/646
[58] Field of Search ........................ 514/272, 646

[56] References Cited

U.S. PATENT DOCUMENTS

| | | | |
|---|---|---|---|
| 4,515,948 | 5/1985 | Kompis et al. | 514/272 |
| 4,587,341 | 5/1986 | Roth et al. | 544/324 |
| 4,590,271 | 5/1986 | Daluge et al. | 544/324 |
| 4,599,416 | 7/1986 | Kompis | 514/272 |

FOREIGN PATENT DOCUMENTS

| | | | |
|---|---|---|---|
| 92/08461 | 5/1992 | WIPO | 514/646 |

OTHER PUBLICATIONS

The Merck Index, 9th ED, Merck & Co, Rahway, N.J., 1976, p. 370 (No. 2808).

"Dictionary of Microbiology", Ed. Japan Association for Microbiology, pp. 742 & 809. Gihodo (Publisher) 1989. only p. 742, lines 32–34 and p. 809, lines 30–32.

"New Pharmacology", Eds. Chikako Tanaka and Ryuichi Kato, pp. 517–518 & 523. Nankodo (Publisher) 1990. only p. 521, line 13 and 25–32 p. 523, lines 2–7.

Derwent Abstract No. AN 830–839071/50. (1982).

Derwent Abstract No. AN 82–02244E/02. (1983).

Carr, A., et al., *J. Acquired Immun. Deficiency Syndrtomes*, 6 (Suppl. 1), S56–S60 (1993).

Cohen, C., Silenzio, U.M.B., *Drug Therapy*, 23 pp. 38–40, 45–46, 49 (1993).

Ruf, B., et al., *Eur. J. Clin. Microbiol. Infect. Dis.*, 12, pp. 325–329 (1993).

Sattler, F. R., *J. Inf. Dis*, 170, pp. 165–172 (1994).

Haile, L.G., Flaherty, J.F., *Ann. Pharmacother.* 12, pp. 1488–1494 (1993).

Elion, Gertrude B., et al., *J. Biol. Chem.*, 208, pp. 477–488 (1954).

*Primary Examiner*—Jerome D. Goldberg
*Attorney, Agent, or Firm*—George W. Johnston; Dennis P. Tramaloni; Alan P. Kass

[57] ABSTRACT

Pharmaceutical preparations containing an antibacterially-active synergistic combination of epiroprim and dapsone are useful in the treatment or control of infections caused by mycobacteria, Actinomycetes and toxoplasmosis pathogens.

6 Claims, No Drawings

ANTIBIOTIC COMBINATION

The present invention is concerned with an antibiotically-active synergistic combination preparation consisting of 2,4-diamino-5-[3,5-diethoxy-4-(pyrrol-1-yl) benzyl]pyrimidine (epiroprim) and 4,4'-diamino-diphenylsulphone (dapsone) or their respective pharmaceutically acceptable salts. The invention is also concerned with the use of epiroprim and dapsone or their respective pharmaceutically acceptable salts as active substances in the treatment or control of infections caused by mycobacteria, Actinomycetes, especially Nocardia sp., and toxoplasmosis pathogens in mammals, both human and non-human, and unit dosage forms containing epiroprim and dapsone to treat or control infections caused by mycobacteria, Acetinomycetes, especially Nocardia sp., and toxoplasmosis pathogens in mammals, both human and non-human.

The use of diaminobenzylpyrimidines, including epiroprim, optionally in combination with dapsone or antibacterially-active sulphonamides, against infections with the fungus *Pneumocystitis carinii* is known from Patent Publication WO 92 08461. It has surprisingly been found that the combination of epiroprim with dapsone is suitable for the treatment of infections in mammals, both human and non-human, caused by mycobacteria, especially *M. marinum*, *M. smegmatis*, *M. avium* and *M. leprae*; and of toxoplasmosis pathogens, especially *Toxoplasma gondii*; as well as Actinomycetes, especially Nocardia sp.

The active substances, epiroprim and dapsone, can be administered individually or as a combination preparation, and simultaneously or chronologically spaced, with the simultaneous administration being preferred. Of course, the method or methods of administration should be done so long that the antibacterially-active synergistic combination of epiroprim and dapsone is ultimately dosed to the mammal in need of treatment.

The active substances can be administered to the mammal in need of treatment either enterally, parenterally or topically. Tablets, capsules, dragées, syrups, suspensions, solutions and suppositories and the like are examples suitable for enteral administration. Infusion or injection solutions and the like are suitable examples for parenteral administration. Creams, lotions, ointments, tinctures, sprays, solutions, and the like are examples suitable for topical administration.

The dosages in which the active substances are administered can vary according to the mode of use and route of use and on the requirements of the patients. The mode of use and route of administration are such that they can be determined by those of ordinary skill in the art based on the patient's requirements.

The active substances can be used in the ratio of about 1:100 to about 100:1 parts by weight epiroprim:dapsone for the treatment or control of the previously named infections or pathogens.

An epiroprim:dapsone ratio of about 1:1 to about 1:5 parts by weight is preferred in the treatment or control of infections caused by mycobacteria. A ratio of about 1:2 to 2:1 is preferred in the treatment or control of infections caused by toxoplasma pathogens. An epiroprim:dapsone ratio of about 4:1 to about 1:1 parts by weight is preferred in the treatment or control of Nocardia infections.

In the case of oral administration, the dosage of the active substances conveniently amounts to about 0.5 to 50 mg/kg body weight per day, preferably 0.5–3 mg/kg body weight per day, for epiroprim; and about 0.5–2 mg/kg body weight per day for dapsone. Dosages for parenteral and topical administration are with the purview of those of ordinary skill in the art. Of course, those skilled in the art will be able to determine the amounts necessary for treatment or control of the infection based on the indicated patient's needs.

In dosage forms, for example tablets, the active substances can be present for example in amounts about of 20–200 mg of epiroprim and about 20–100 mg of dapsone per tablet. Other dosage forms and the amounts of active substances are within the purview of those of ordinary skill in the art.

The pharmaceutical preparations can contain inert carriers or substances or pharmacodynamically active additives. Tablets or granulates for example, can contain a series of binders, fillers, carriers or diluents. Liquid preparations can be present, for example, in the form of a sterile, water-miscible solution. Besides the active substance, capsules can additionally contain a filler or thickener. Furthermore, flavor-improving additives as well as substances usually used as preservatives, stabilizers, moisture retainers and emulsifiers as well as salts for varying the osmotic pressure, buffers and other additives can be present.

The previously mentioned carriers and diluents can comprise organic or inorganic substances, for example water, gelatin, lactose, starch, magnesium stearate, talc, gum arabic, polyalkylene glycols and the like. It is a prerequisite that all adjuvants used in the making of the pharmaceutical preparations are non-toxic.

For topical administration the active substances are conveniently used in the form of ointments, tinctures, creams, solutions, lotions, sprays, suspensions and the like. Ointments and creams as well as solutions are preferred. These preparations intended for topical administration can be manufactured by admixing the process products as active ingredients with non-toxic, inert, solid or liquid carriers which are suitable for topical treatment and which are usual in such preparations.

Conveniently, about 0.1–5%, preferably 0.3–2%, solutions as well as about 0.1–5%, preferably about 0.3–2%, ointments or creams are suitable for topical administration.

If desired, an antioxidant, for example tocopherol, N-methyl-γ-tocopheramine as well as t-butyl-hydroxyanisole or t-butyl-hydroxytoluene, can be admixed with the preparations.

The activity of the combination preparation in accordance with the invention will be evident from the data presented in the following Tables.

Tables 1 and 2 give the in vitro activity of the active substances alone and in combination as the minimum inhibitory concentration (MIC) for various mycobacteria and Actinomycetes strains as well as the FIC (fractionary inhibitory concentration) index, which is a measurement of the synergistic effect (see J. Biol. Chem. 1954, 208, 477). The smaller the FIC index, the greater the synergistic effect.

Table 3 shows the percentage inhibition of *M. lufu* cultures, which is a recognized model for testing drugs against leprosy, achieved with certain concentrations of the individual active substances and their combined administration.

Tables 4 and 5 show the in vivo activity in the case of Nocardia and Toxoplasma infections. The experimental animals were infected i.p. with 10,000 colony-forming units of the pathogen RH *Toxoplasma gondii*. Twenty-four hours after the infection, the indicated active substance doses were administered to the animals through a probang twice daily for 14 days. "Cured" denotes animals without detectable cysts in the brain.

TABLE 1

Checkerboard titration against various mycobacteria

| | MIC alone | | MIC in combination | | |
|---|---|---|---|---|---|
| Pathogen | Dapsone [μg/ml] | Epiroprim [μg/ml] | Dapsone + Epiroprim [μg/ml] | | FIC indices |
| M. avium SN 304 | >30 | >30 | 6 | 15 | <0.7 |
| | | | 3 | 18 | <0.7 |
| M. intracellulare SN 403 | >30 | 8 | 3 | 1 | >0.23 |
| M. kansasii | >20 | >20 | 8 | 10 | <0.9 |
| | | | 6 | 11 | <0.9 |
| M. lufu L 209 | 0.012 | >6 | 0.002 | 1.2 | <0.36 |
| M. marinum SN 1254 | 3 | 16 | 0.5 | 2 | ≦0.3 |
| M. smegmatis ATCC 607 | 0.4 | 2.5 | 0.08 | 0.5 | ≦0.4 |

TABLE 2

In vitro activity against Actinomycetes

| | Incubation | MIC alone | | MIC in combination | | |
|---|---|---|---|---|---|---|
| Pathogen | time (days) | Dapsone [μg/ml] | Epiroprim [μg/ml] | Dapsone + epiroprim [μg/ml] | | FIC indices |
| Nocardia asteroides N1 | 3 | >100 | 100 | 3.125 | 3 | 0.0625 |
| | 7 | >100 | >100 | 6 | 6 | 0.125 |
| Nocardia asteroides N10 | 3 | 25 | 25 | <3 | <3 | <0.25 |
| | 7 | 50 | 50 | 3 | 3 | 0.125 |
| Nocardia brasiliensis N2 | 7 | 12.5 | >100 | 6.25 | 6.25 | 0.53 |
| Streptomyces sp. N31 | 3 | >100 | 25 | 3 | 6 | <0.281 |
| | 7 | >100 | 100 | 3 | 12 | <0.186 |
| Actinomadura madurae N3 | 7 | >100 | >100 | 50 | 50 | <0.5 |

TABLE 3

Combination of epiroprim with dapsone in vitro against Mycobacterium lufu

| | μg/ml | % inhibition |
|---|---|---|
| Epiroprim | 5 | 14 |
| | 25 | 34 |
| | 60 | 73 |
| Dapsone | 0.2 | 22 |
| | 0.4 | 22 |
| Epiroprim + dapsone | 5 + 0.2 | 84 |
| | 25 + 0.4 | 96 |

TABLE 4

Activity in vivo against nocardiosis in mice

| Dosage [mg/kg] | | | Average survival period |
|---|---|---|---|
| Dapsone | Epiroprim | % Survivors | (days) |
| 1 | — | 0 | 2.6 |
| — | 30 | 0 | 1.7 |
| — | 100 | 0 | 2 |
| 1 | 30 | 20 | 6.6 |
| 1 | 100 | 40 | 13.2 |
| 3 | 30 | 60 | 12.2 |
| 3 | 100 | 100 | >20 |

TABLE 5

In vivo activity against toxoplasmosis

| | Dosage (mg) | Number of survivors | Cured animals in % of survivors |
|---|---|---|---|
| Dapsone | 50 | 1/10 | 0 |
| Dapsone | 100 | 10/10 | 0 |
| Epiroprim | 100 | 0/10 | — |
| Epiroprim/ | 25/25 | 0/10 | |
| Dapsone | 50/50 | 10/10 | 30 |
| | 100/50 | 10/10 | 20 |
| | 100/100 | 10/10 | 50 |
| Control | 0/30 | 0/30 | |

The active substance combination in accordance with the invention can be used for example for the treatment of nocardioses, actinomycetoses and mycetomas caused by Actinomycetes such as *Actinomyces israeli*, *A. naeslundii* etc, *Norcardia brasiliensis*, *N. asteroides* etc and by Streptomycetes such as *Streptomyces madurae*, *S. someliensis*, *S. pelletieri*, *Madurella mycetomi*; generalized infections with mycobacteria, especially those with *M. avium* and *M. intracellulare* in patients (mammals, both human and non-human) with damaged functions of the immune system; as well as for the treatment of leprosy and cerebral toxoplasmosis.

The following is an example of a typical dosage form:

| Tablets: | |
|---|---|
| Dapsone | 100 mg |
| Epiroprim | 200 |
| PRIMOJEL (starch derivative) | 6 |
| Povidone K 30 (polyvinylpyrrolidone) | 8 |
| Magnesium stearate | 6 |
| Total weight | 320 mg |

We claim:

1. A pharmaceutical composition comprising antibacterially active synergistic amounts of 2,4-diamino-5-[3,5-diethoxy-4-(pyrrol-1-yl)benzyl]pyrimidine (epiroprim) and 4,4'-diamino-diphenylsulphone (dapsone) or their respective pharmaceutically acceptable salts, and an inert carrier, which are used in the treatment or control of infections caused by mycobacteria wherein the amounts of epiroprim and dapsone are in the ratio of about 6:1 (epiroprim:dapsone) to about 1:60 (epiroprim:dapsone) parts by weight.

2. A pharmaceutical composition comprising antibacterially active synergistic amounts of 2,4-diamino-5-[3,5-diethoxy-4-(pyrrol-1-yl)benzyl]pyrimidine (epiroprim) and 4,4'-diamino-diphenylsulphone (dapsone) or their respective pharmaceutically acceptable salts, and an inert carrier, which are used in the treatment or control of infections caused by actinomycetes wherein the amounts of epiroprim and dapsone are in the ratio of about 4:1 (epiroprim:dapsone) to about 1:1 (epiroprim:dapsone) parts by weight.

3. A pharmaceutical composition comprising antibacterially active synergistic amounts of 2,4-diamino-5-[3,5-diethoxy-4-(pyrrol-1-yl)benzyl]pyrimidine (epiroprim) and 4,4'-diamino-diphenylsulphone (dapsone) or their respective pharmaceutically acceptable salts, and an inert carrier, which are used in the treatment or control of infections caused by toxoplasmosis pathogens wherein the amounts of epiroprim and dapsone are in the ratio of about 1:1 (epiroprim:dapsone) to about 2:1 (epiroprim:dapsone) parts by weight.

4. A method for treating infections in a mammal having infections caused by mycobacteria which comprises administering to said mammal in need of such treatment a pharmaceutical composition comprising antibacterially-active synergistic amounts of 2,4-diamino-5-[3,5-diethoxy-4-(pyrrol-1-yl)benzyl]pyrimidine (epiroprim) and 4,4'-diamino-diphenylsulphone (dapsone) or their respective pharmaceutically acceptable salts, and an inert carrier, in an amount which is effective in treating infections caused by mycobacteria, wherein the amounts of epiroprim and dapsone are in the ratio of about 6:1 (epiroprim:dapsone) to about 1:60 (epiroprim:dapsone) parts by weight.

5. A method for treating infections in a mammal having infections caused by mycobacteria which comprises administering to said mammal in need of such treatment a pharmaceutical composition comprising antibacterially active synergistic amounts of 2,4-diamino-5-[3,5-diethoxy-4-(pyrrol-1-yl)benzyl]pyrimidine (epiroprim) and 4,4'-diamino-diphenylsulphone (dapsone) or their respective pharmaceutically acceptable salts, and an inert carrier, which is effective in treating infections caused by actinomycetes wherein the amounts of epiroprim and dapsone are in the ratio of about 4:1 (epiroprim:dapsone) to about 1:1 (epiroprim:dapsone) parts by weight.

6. A method for treating infections in a mammal having infections caused by mycobacteria which comprises administering to said mammal in need of such treatment a pharmaceutical composition comprising antibacterially active synergistic amounts of 2,4-diamino-5-[3,5-diethoxy-4-(pyrrol-1-yl)benzyl]pyrimidine (epiroprim) and 4,4'-diamino-diphenylsulphone (dapsone) or their respective pharmaceutically acceptable salts, and an inert carrier, which is effective in treating infections caused by toxoplasmosis pathogens wherein the amounts of epiroprim and dapsone are in the ratio of about 1:1 (epiroprim:dapsone) to about 2:1 (epiroprim:dapsone) parts by weight.

* * * * *